US00PP31452P2

(12) United States Plant Patent
Lannes

(10) Patent No.: US PP31,452 P2
(45) Date of Patent: Feb. 18, 2020

(54) ***HIBISCUS* PLANT NAMED 'LANWYACONDA'**

(50) Latin Name: *Hibiscus rosa-sinensis*
Varietal Denomination: Lanwyaconda

(71) Applicant: D.H.M. INNOVATION, Malause (FR)

(72) Inventor: Robert M. Lannes, Malause (FR)

(73) Assignee: D.H.M. INNOVATION, Malause (FR)

( * ) Notice: Subject to any disclaimer, the term of this patent is extended or adjusted under 35 U.S.C. 154(b) by 0 days.

(21) Appl. No.: 16/501,420

(22) Filed: Apr. 10, 2019

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ..... A01H 5/02; A01H 6/60
See application file for complete search history.

*Primary Examiner* — Annette H Para
(74) *Attorney, Agent, or Firm* — Penny J. Aguirre

(57) ABSTRACT

A new cultivar of *Hibiscus* plant named 'Lanwyaconda' that is characterized by its uniform flowers that are shades of pink in color being darker pink in the centers and becoming light rose on the edge of the petals, its flower petals with wavy and curled edges, its floriferous habit with flowers that last open over 3 days, its early blooming and freely flowering habit, its strong flowering stems with upright facing flowers, its compact and self-branching plant habit, and its foliage that is resistant to pathogens common to *Hibiscus*, including *Pseudomonas* sp., *Phythium* sp., and *Phytophthora* sp.

2 Drawing Sheets

Botanical classification: *Hibiscus rosa-sinensis.*
Cultivar designation: 'Lanwyaconda'.

CROSS REFERENCE TO A RELATED APPLICATIONS

This application is related U.S. Plant Patents for plants derived from the same breeding program that are entitled *Hibiscus* Plant Named 'Lanlampasas' (U.S. Plant Pat. No. 25,660) and *Hibiscus* Plant Named 'Lansabine' (U.S. Plant Pat. No. 25,662).

BACKGROUND OF THE INVENTION

The present invention relates to a new and distinct cultivar of *Hibiscus rosa-sinensis* named 'Lanwyaconda' and will be referred to hereafter by its cultivar name, 'Lanouachita'. 'Lanwyaconda' is a new cultivar of tropical *hibiscus* grown for use as a landscape and container plant.

The new cultivar was developed through an ongoing breeding program conducted by the Inventor in Malause, France. The objectives of the breeding program are to develop new cultivars of *Hibiscus* that exhibit brightly colored unique flowers, self-branching, high flower bud counts, and compact plant habits.

'Lanwyaconda' arose from a cross made by the Inventor in July of 2011 between *Hibiscus rosa-sinensis* 'Lanlampasas' as the male parent and an unnamed plant of *Hibiscus rosa-sinensis* from the breeding program, reference no. si 1135-1. 'Lanwyaconda' was selected as a single unique plant from the resulting seedlings in June of 2012.

Asexual propagation of the new cultivar was first accomplished by the Inventor by stem cuttings in July of 2014 in Malause, France. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Lanwyaconda' as a new and distinct cultivar of *Hibiscus.*

1. 'Lanwyaconda' exhibits uniform flowers that are shades of pink in color being darker pink in the centers and becoming light rose on the edge of the petals.
2. 'Lanwyaconda' exhibits flower petals with wavy and curled edges.
3. 'Lanwyaconda' exhibits a floriferous habit with flowers that last open over 3 days.
4. 'Lanwyaconda' exhibits an early blooming and freely flowering habit.
5. 'Lanwyaconda' exhibits strong flowering stems with upright facing flowers.
6. 'Lanwyaconda' exhibits a compact and self-branching plant habit.
7. 'Lanwyaconda' exhibits foliage that is resistant to pathogens common to *Hibiscus*, including *Pseudomonas* sp., *Phythium* sp., and *Phytophthora* sp.

The female parent of 'Lanchippewa', 'Lanlampasas', is similar to 'Lanwyaconda' in being floriferous all season. 'Lanlampasas' differs from 'Lanwyaconda' in having flowers that are light orange in color with a large pink center with softer petals that lack curled edges, a lower flower bud count, and in having a less compact plant habit. The male parent of 'Lanwyaconda' differs from 'Lanwyaconda' in having much smaller flowers that do not remain open very long. 'Lanwyaconda' can also be compared to the *Hibiscus* cultivar 'Lansabine'. 'Lansabine' is similar to 'Lanwyaconda' in having glossy foliage that tolerates heat and sun well and in having large-sized flowers. 'Lansabine' differs from 'Lanwyaconda' in having flowers that are rose in color that remain open 1 to 2 days with softer petals, and in having a less compact plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Hibiscus*. The photographs were taken of a 15-month-old plant of 'Lanwyaconda' as grown in a two-gallon container in Malause, France.

The photograph in FIG. 1 provides a side view of 'Lanwyaconda' in bloom.

Figure 1:
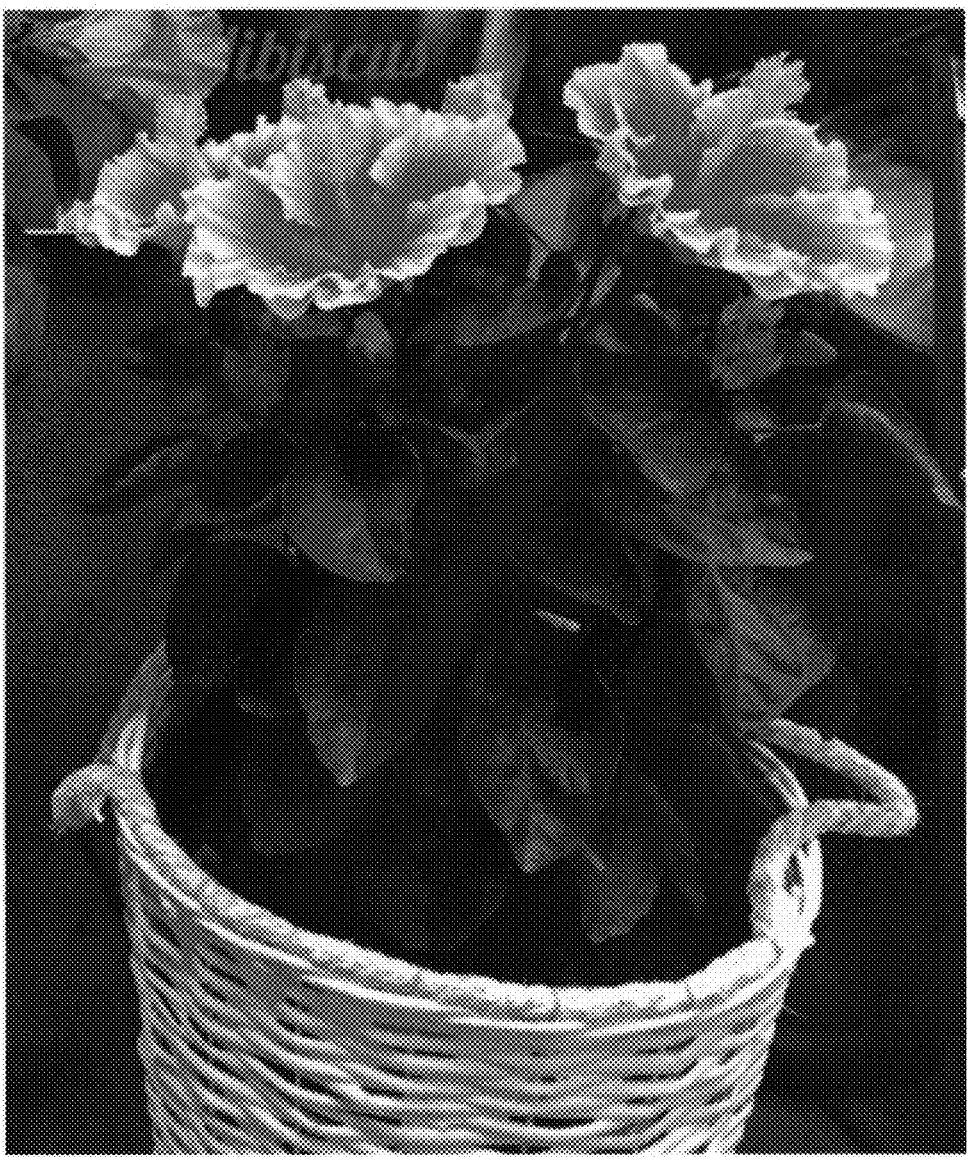
Figure 2:
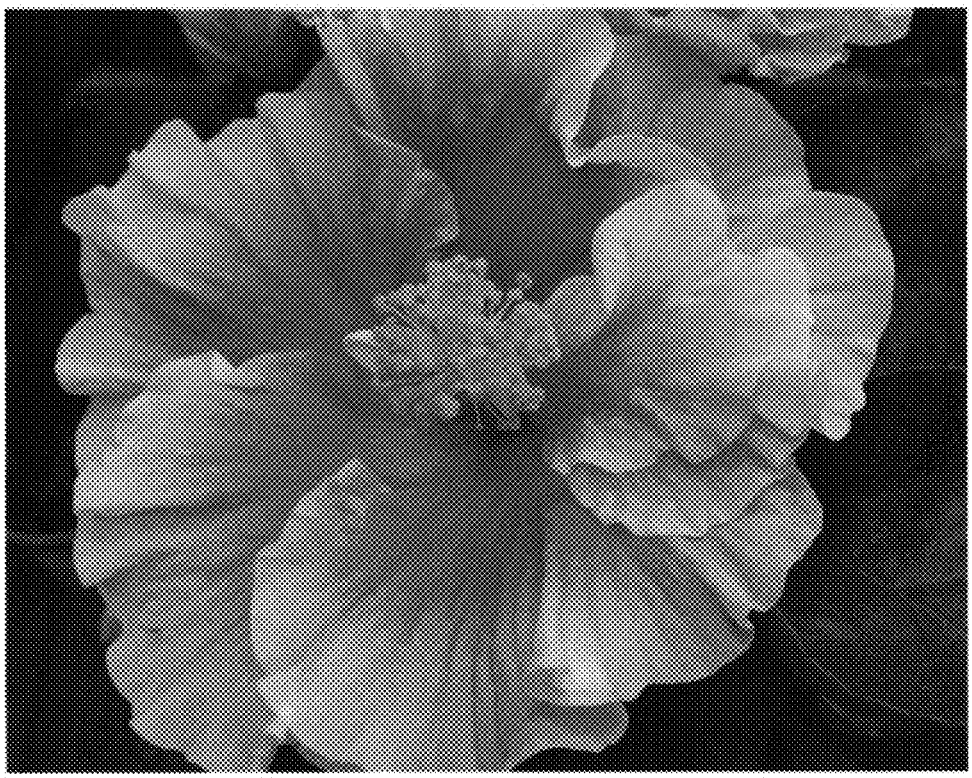

The photograph in FIG. 2 provides a close-up view of a flower of 'Lanwyaconda'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 15-month-old plants of the new cultivar as grown in one-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

- *Blooming period*.—Continuously producing in warm temperatures 55° F. to 90° F. in France.
- *Plant type*.—Tropical evergreen shrub.
- *Plant habit*.—Moderately upright, compact and self-branching plant habit.
- *Height and spread*.—An average of 37 cm in height and 45 cm in spread as grown in a one gallon container, reaching an average of 1.2 m in height and 1.5 m in width in the landscape.
- *Hardiness*.—Tropical; at least in U.S.D.A. Zones 9 to 10.
- *Diseases*.—Resistance to pathogens common to *Hibiscus*, including *Pseudomonas* sp., *Phythium* sp., and *Phytophthora* sp.
- *Root description*.—Fibrous roots, 161A in color.
- *Propagation*.—Stem cuttings.
- *Root development*.—Roots initiate in about 20 days and develop as a young plant in about 2 months.
- *Growth rate*.—Moderately vigorous.

Stem description:

- *Shape*.—Slightly oval.
- *Stem color*.—New growth; 146A, mature wood; 199D with striations of 197A.
- *Stem size*.—Main stem; 10 cm in length, 1.5 cm in diameter, lateral branches; average of 35 cm in length and 5 mm in width.
- *Stem surface*.—New growth; sparsely pubescent, very shiny, mature wood; finely striated and rugose.
- *Stem aspect*.—Held in multiple angles.
- *Stem strength*.—Strong.
- *Branching*.—An average of 10 lateral branches.
- *Internode*.—Ranges between 1 and 4 cm.
- *Stipules*.—2 per upper leaf node, linear to narrowly lanceolate in shape, an average of 6 mm in length and 0.5 mm in width, glabrous surface, acuminate apex, truncate base, 144A in color.

Foliage description:

- *Leaf shape*.—Deltoid to cordate.
- *Leaf division*.—Simple.
- *Leaf base*.—Truncate.
- *Leaf apex*.—Acute to bluntly acute.
- *Leaf venation*.—Pinnate, matches leaf surfaces.
- *Leaf margins*.—Serrate and slightly wavy, tips of serration have a small mucronate tip.
- *Leaf attachment*.—Petiolate.
- *Leaf arrangement*.—Alternate.
- *Leaf orientation*.—Slightly upward to horizontal to slightly downward to petiole.
- *Leaf aspect*.—Primarily flat with slightly wavy margins.
- *Leaf surface*.—Upper surface glabrous and glossy, lower surface glabrous and matte.
- *Leaf color*.—Young leaves upper and lower surface; 144A, mature leaves upper surface; 147A, mature leaves lower surface; 147B.
- *Leaf size*.—An average of 9 cm in length and 7 cm in width when mature.
- *Leaf quantity*.—An average of 16 per branch.
- *Petioles*.—An average of 3 cm in length and 2 mm in diameter, 145A in color, finely pubescent surface.

Flower description:

- *Inflorescence type*.—Flowers are solitary from upper leaf axils.
- *Lastingness of flowers*.—An average of 2 to 3 days, self cleaning.
- *Flower size*.—An average of 10 cm in depth and 15 cm in diameter (including calyx).
- *Flower fragrance*.—None.
- *Flower shape*.—Rotate.
- *Flower number*.—Average of 3 per lateral stem.
- *Flower aspect*.—Outward to slightly upright.
- *Flower bud*.—Elliptic in shape, an average of 4 cm in length and 2 cm in width, a blend of 62A and 62C in color with a light flush of 18B, glabrous and shiny surface.
- *Petals*.—5, 5% fused, 40% overlapping, oblanceolate in shape, an average of 7 cm in length and 10 cm in width, wavy and curled margins, rounded apex, base is cuneate slightly oblique and adnate to base of style re-curved, lower surface is dull, upper surface; satiny and waxy near the base (throat), color upper surface when opening and fully open; tips 69C with a very faint flush of 13D, mid-section 58B blending into base and becoming a blend of 58B and 47A, veins turning from 69C at the base to mid section to N66A at the tips, color lower surface when opening and when fully open; a blend of 62A and 62C in color and lightly flushed with 18B at the edges.

*Calyx*.—Campanulate in shape, average of 3 cm in length and 2 cm in diameter.

*Epicalyx*.—Comprised of 6 bracts held upright surrounding sepals, lanceolate in shape, acute apex, truncate base, average of 1.3 cm in length and 5 mm in width, color of both surfaces is a blend of 145A and 146A with base 145A, outer surface dull, inner surface glossy.

*Sepals*.—5, base 50% fused, an average of 3 cm in length and 1.5 cm in width, color of both surfaces is a blend of 143A and N144A, outer surface is puberulent and inner surface is glossy and smooth, acute apex, truncate base.

*Peduncles*.—An average of 4 cm in length and 3 mm in diameter, strong, average angle upright to outward, 144A in color, glabrous and slightly glossy surface.

*Pedicels*.—Not present, flowers are solitary from terminal leaf axils.

*Receptacle*.—1.5 mm in diameter, 145A in color, glabrous and glossy surface.

Reproductive organs:

*Gynoecium*.—Pistil; 1, 5.5 cm in length, stigmas; 5, round in shape, 5 mm in diameter, 2 mm in depth, surface densely covered with short fuzzy hairs, color 13A and 8A, style arms; 3 mm in length, 1 mm in width, 8C in color, surface is glabrous and glossy, style; average of 4.5 cm in length and 4 mm in width, smooth and glossy surface, color a blend of 8C in color flushing with 47B at the base, ovary; orbicular in shape with round apex, 1 cm in length, 5 mm width, 7A in color.

*Androecium*.—Stamens; average of 50, 5 mm in length, stamens are clustered and implanted into upper portion of style, anthers; dorsifixed and curled in shape, 2 mm in diameter, 2 mm in depth, color 10B, filament; 4 mm in length, color 8C, pollen; abundant in quantity and 17B in color.

*Fruit/seeds*.—None observed to date.

It is claimed:

1. A new and distinct cultivar of *Hibiscus* plant named 'Lanwyaconda' as herein illustrated and described.

* * * * *